(12) United States Patent
Kitagawa et al.

(10) Patent No.: US 8,562,518 B2
(45) Date of Patent: Oct. 22, 2013

(54) FLEXIBLE ENDOSCOPE PART

(75) Inventors: Hideya Kitagawa, Hachioji (JP); Yoshiaki Ito, Fuchu (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/421,477

(22) Filed: Mar. 15, 2012

(65) Prior Publication Data

US 2012/0170970 A1     Jul. 5, 2012

Related U.S. Application Data

(63) Continuation of application No. PCT/JP2010/065904, filed on Sep. 15, 2010.

(30) Foreign Application Priority Data

Sep. 17, 2009   (JP) ................................. 2009-216129

(51) Int. Cl.
    *A61B 1/008*      (2006.01)

(52) U.S. Cl.
    USPC .............................. 600/142; 600/146; 403/54

(58) Field of Classification Search
    USPC ............ 600/228, 229, 141, 142, 146; 403/53, 403/54, 57, 58, 150, 209, 213
    See application file for complete search history.

(56) References Cited

U.S. PATENT DOCUMENTS

| | | | | |
|---|---|---|---|---|
| 3,220,677 | A | * | 11/1965 | Sweeney ...................... 403/213 |
| 4,108,211 | A | * | 8/1978 | Tanaka ........................... 600/142 |
| 4,432,349 | A | * | 2/1984 | Oshiro .......................... 600/141 |
| 4,834,069 | A | * | 5/1989 | Umeda ......................... 600/142 |
| 5,179,935 | A | * | 1/1993 | Miyagi ......................... 600/142 |
| 5,271,382 | A | * | 12/1993 | Chikama ....................... 600/142 |
| 6,454,703 | B1 | * | 9/2002 | Ide ................................ 600/142 |
| 6,482,149 | B1 | | 11/2002 | Torii |
| 6,641,528 | B2 | * | 11/2003 | Torii ............................. 600/142 |
| 6,793,436 | B1 | * | 9/2004 | Ruel et al. ..................... 403/213 |
| 7,806,619 | B2 | * | 10/2010 | Bodtker .......................... 403/53 |
| 2006/0126177 | A1 | | 6/2006 | Kim et al. |
| 2007/0225565 | A1 | | 9/2007 | Ogino |

FOREIGN PATENT DOCUMENTS

| | | | |
|---|---|---|---|
| JP | 56-138601 | | 10/1981 |
| JP | 58-46801 | Y2 | 10/1983 |
| JP | 62-79003 | A | 4/1987 |
| JP | 1-120804 | U | 8/1989 |

(Continued)

OTHER PUBLICATIONS

International Search Report dated Nov. 2, 2010 (in English) in counterpart International Application No. PCT/JP2010/065904.

(Continued)

*Primary Examiner* — Michael P Ferguson
(74) *Attorney, Agent, or Firm* — Holtz, Holtz, Goodman & Chick, PC

(57) ABSTRACT

A flexible endoscope part including an operation member pulling operated to curve a flexible part, a plurality of joint rings connected substantially coaxially to be pivot-able in relation to each other, each the joint rings have an opening part and an engagement part, and an operation-member receiving unit which is inserted into the opening part from outside to inside in the radial direction of the joint ring, is formed by performing bending process on an elastic wire material, is protruded into inside of the joint ring, wherein the operation-member insertion part forms a coil shape which extends in an insertion direction of the operation member.

2 Claims, 14 Drawing Sheets

(56) References Cited

FOREIGN PATENT DOCUMENTS

| JP | 2-261418 A | 10/1990 |
|----|------------|---------|
| JP | 3-26226 A | 2/1991 |
| JP | 3-37031 A | 2/1991 |
| JP | 3-68326 A | 3/1991 |
| JP | 4-158826 A | 6/1992 |
| JP | 6-75403 U | 10/1994 |
| JP | 2000-23908 A | 1/2000 |
| JP | 2000-316800 A | 11/2000 |
| JP | 2007-181600 A | 7/2007 |
| JP | 2007-252448 A | 10/2007 |
| JP | 2008-154809 A | 7/2008 |

OTHER PUBLICATIONS

International Preliminary Report on Patentability (IPRP) dated Apr. 19, 2012 (in English) issued in parent International Application No. PCT/JP2010/065904.

* cited by examiner

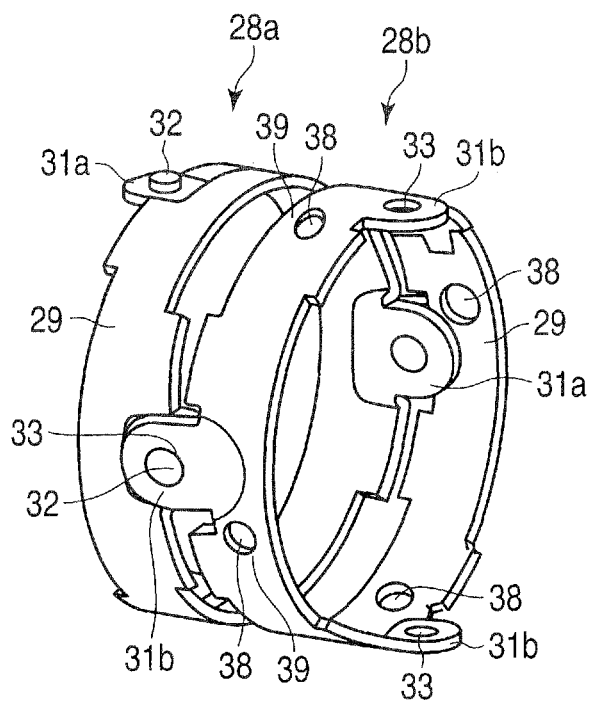
F I G. 4
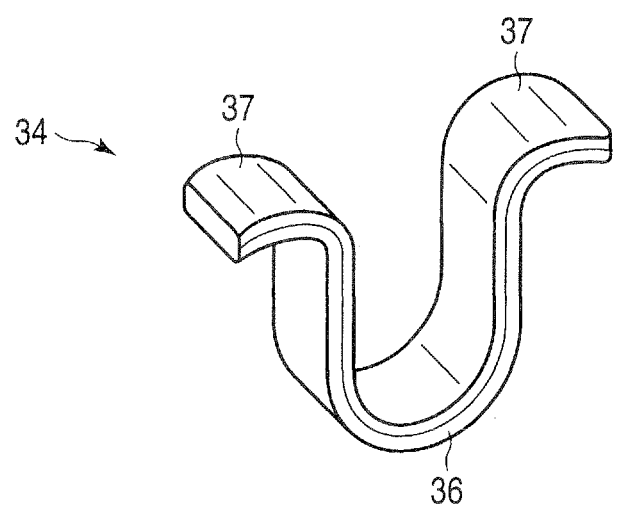
F I G. 5

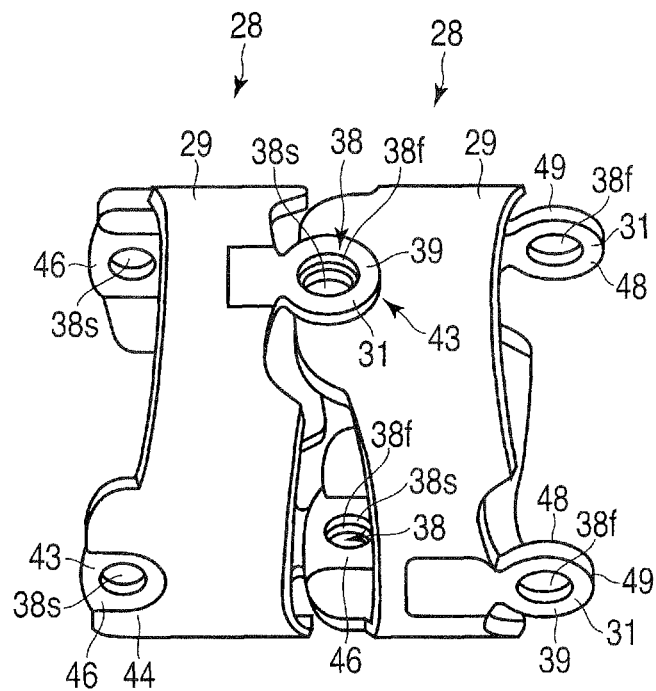
F I G. 10
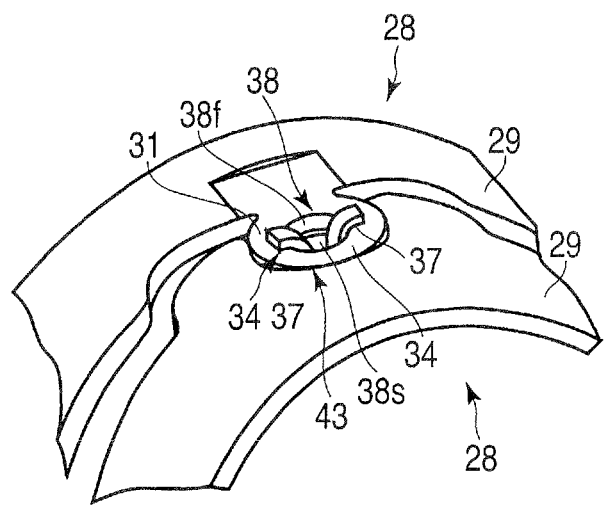
F I G. 11

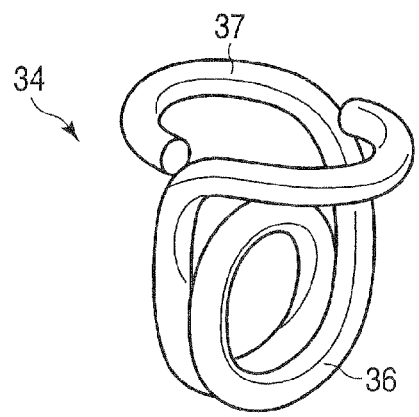
F I G. 18
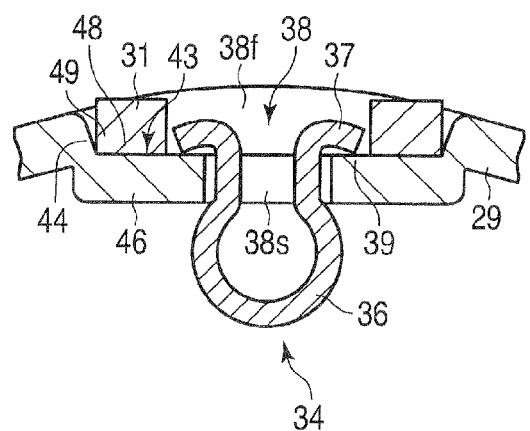
F I G. 19
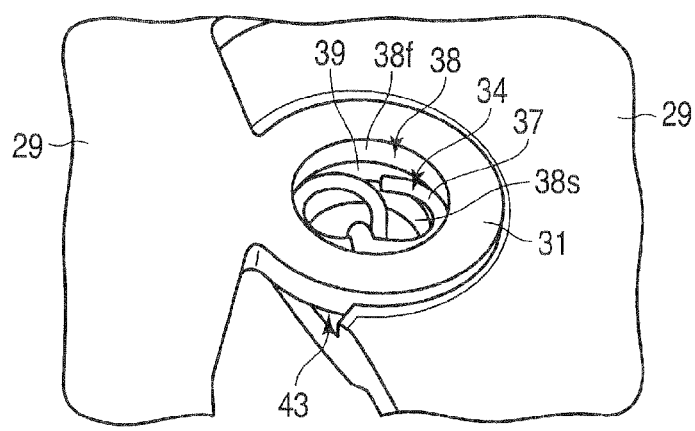
F I G. 20

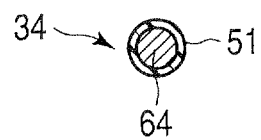
F I G. 21
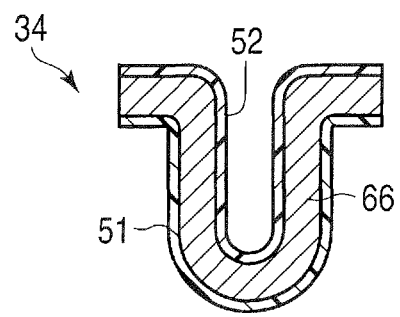
F I G. 22A
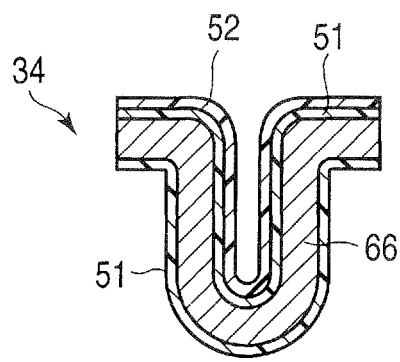
F I G. 22B

FLEXIBLE ENDOSCOPE PART

CROSS REFERENCE TO RELATED APPLICATIONS

This application is a Continuation Application of PCT Application No. PCT/JP2010/065904, filed Sep. 15, 2010 and based upon and claiming the benefit of priority from prior Japanese Patent Application No. 2009-216129, filed Sep. 17, 2009, the entire contents of which are incorporated herein by reference.

BACKGROUND OF THE INVENTION

1. Field of the Invention

The present invention relates to a flexible endoscope part.

2. Description of the Related Art

An endoscope comprises an insertion part which is inserted into a tubular cavity, and a flexible part which is operated to curve is provided at a top end of the insertion part. The flexible part comprises a flexible tube which forms a skeletal structure of the flexible part.

Jpn. UM Appln. KOKOKU Publication No. 38-46801 discloses a flexible tube. In the flexible tube, number of joint rings are substantially coaxially connected sequentially in a mariner that the joint rings are pivotable in relation to each other.

Specifically, in the joint rings each, a pair of tongue parts is provided to protrude at each of two ends of a cylindrical part. An axial hole is formed to penetrate each tongue part in a radial direction. For each two adjacent joint rings, a pair of tongue parts of one of the adjacent joint rings and a pair of tongue parts of the other of the adjacent joint rings are layered on each other in radial directions, and a joint shaft is inserted through the axial holes of the tow pairs of tongue parts. The joint shafts each are provided with a pair of gap parts extending throughout a whole circumference of the joint shaft substantially in radial directions of the joint shaft. Two tongue parts are sandwiched by both gap parts of the joint shaft, to be pivotable in relation to each other about the joint axes each. Further, inner ends of each joint shaft in the radial directions are protruded to inside of the joint rings. Wire insertion holes are formed to penetrate the inner ends of the joint shafts in the radial directions of the flexible tube. Angle wires are inserted through the wire insertion holes, and top ends of the angle wire are fixed to the top ends of the insertion part. The flexible part can be operated to curve by pulling/operating the angle wire.

In the flexible tube according to Jpn. UN Appln. KOKOKU Publication No. 58-46801, the joint shafts each are formed of a rigid member and do not substantially deform. Therefore, when the flexible part is operated to curve by pulling/operating the angle wires, there is a case that resistance against a pulling operation of the angle wires increases and causes difficulties in smoothly operating the flexible part, depending on a positional relationship between the angle wires and the joint shafts and conditions of load from the angle wires to the joint shafts. In addition, the joint shafts each are formed by cutting/processing a rod-type rigid material, and are therefore difficult to manufacture at low costs. Since the pair of gap parts of each joint shaft sandwich two tongue parts, work of attaching the joint shafts to the joint rings is complicated. Therefore, there are difficulties in manufacturing the flexible part at low costs.

The invention has been made in view of the problems as described above and has an object of providing a flexible endoscope part, which can be smoothly operated to curve and can be manufactured at low costs.

BRIEF SUMMARY OF THE INVENTION

According to an embodiment of the present invention, there is provided a flexible endoscope part, comprising: an operation member pulled or operated to curve a flexible part; a plurality of joint rings connected substantially coaxially to be pivotable in relation to each other, the joint rings comprising at least one joint ring comprising an opening part which penetrates the joint ring in a radial direction thereof, and an engagement part formed around the opening part outside of the joint ring in the radial direction thereof; and an operation-member receiving unit which is inserted into the opening part from outside to inside in the radial direction of the joint ring, is formed by performing bending process on an elastic wire material, is protruded into inside of the joint ring, and comprises an operation-member insertion part where the operation member is inserted in, and an engagement part engaged on an engagement receiving part in a manner that the operation-member receiving unit is pivotable in relation to the joint ring about a rotation axis as a center extending in a substantially radial direction of the at least one joint ring, wherein the operation-member insertion part forms a coil shape which extends in an insertion direction of the operation member.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a perspective view showing adjacent two joint rings according to the first embodiment;

FIG. 5 is a perspective view showing a wire receiving member according to the first embodiment of the invention;

FIG. 10 is a perspective view showing adjacent two joint rings according to the second embodiment;

FIG. 11 is a perspective view showing the two adjacent joint rings and the wire receiving member according to the second embodiment of the invention, viewed from outside in a radial direction;

FIG. 18 is a perspective view showing a wire receiving member according to a modification to the third embodiment of the invention;

FIG. 19 is a cross-sectional view showing two adjacent joint rings and a wire receiving member according to the fourth embodiment of the invention;

FIG. 20 is a perspective view showing two adjacent two joint rings and a wire receiving member according to a modification to the fourth embodiment of the invention;

FIG. 21 is a cross-sectional view showing a wire material according to the fifth embodiment of the invention;

FIG. 22A is a cross-sectional view showing a wire receiving member according to the sixth embodiment of the invention;

FIG. 22B is a cross-sectional view showing a wire receiving member according to the first modification to the sixth embodiment of the invention;

DETAILED DESCRIPTION OF THE INVENTION

Embodiments of the invention will be described with reference to the drawings.

Figure 1:
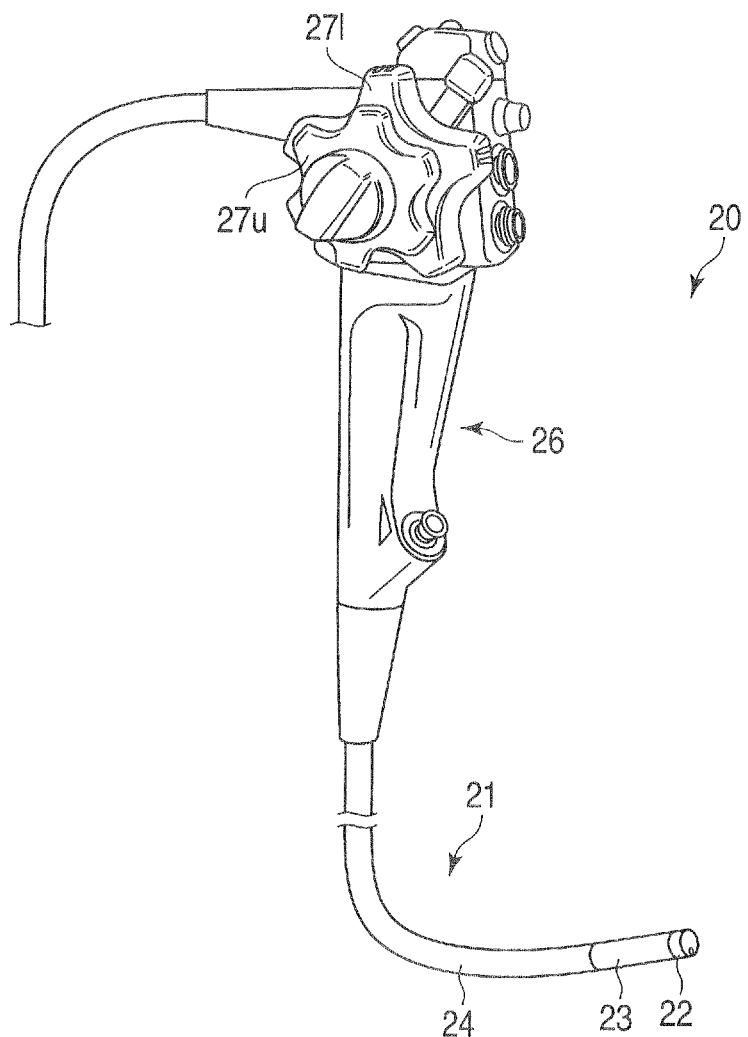
FIG. 1 is a perspective view showing an endoscope according to the first embodiment of the invention.

The first embodiment of the invention will be described with reference to FIGS. 1 to 7. With reference to FIG. 1, an endoscope 20 comprises an insertion part 21 which is inserted into a body cavity. In the insertion part 21, a hard tip end part 22, a flexible part 23 which is operated to curve in upward, downward, leftward, and rightward directions, and a flexible tube part 24 which is long and flexible are provided to be connected from a tip end side to a base end side. An operation part 26 which is held and operated by an operator is connected to a base end part of the insertion part 21.

The operation part 26 is provided with curve operation knobs 27u and 27l for curve operations in upward and downward directions and in leftward and rightward directions to operate the flexible part 23 so as to curve in upward, downward, leftward, and rightward directions.

The curve operation knobs 27u and 27l each are connected to an angle mechanism included in the operation part 26. Angle wires 41 for curve operations in the upward, downward, leftward, and rightward directions, as operation members, are extended from the angle mechanism. Each of the angle wires 41 is introduced from the operation part 26 into the insertion part 21 and is inserted into the insertion part 21.

By rotating the curve operation knob 27u for upward and downward curve operations in a direction or in a reverse direction, the angle wires 41 for upward and downward curve operations are respectively pulled and relaxed or relaxed and pulled. Accordingly, the flexible part 23 is operated to curve in the upward or downward direction. The same description as described above applies also to the leftward and rightward directions.

With reference to FIGS. 2 to 7, a flexible tube unit 25 forming the flexible part 23 will be described.

Figure 2:
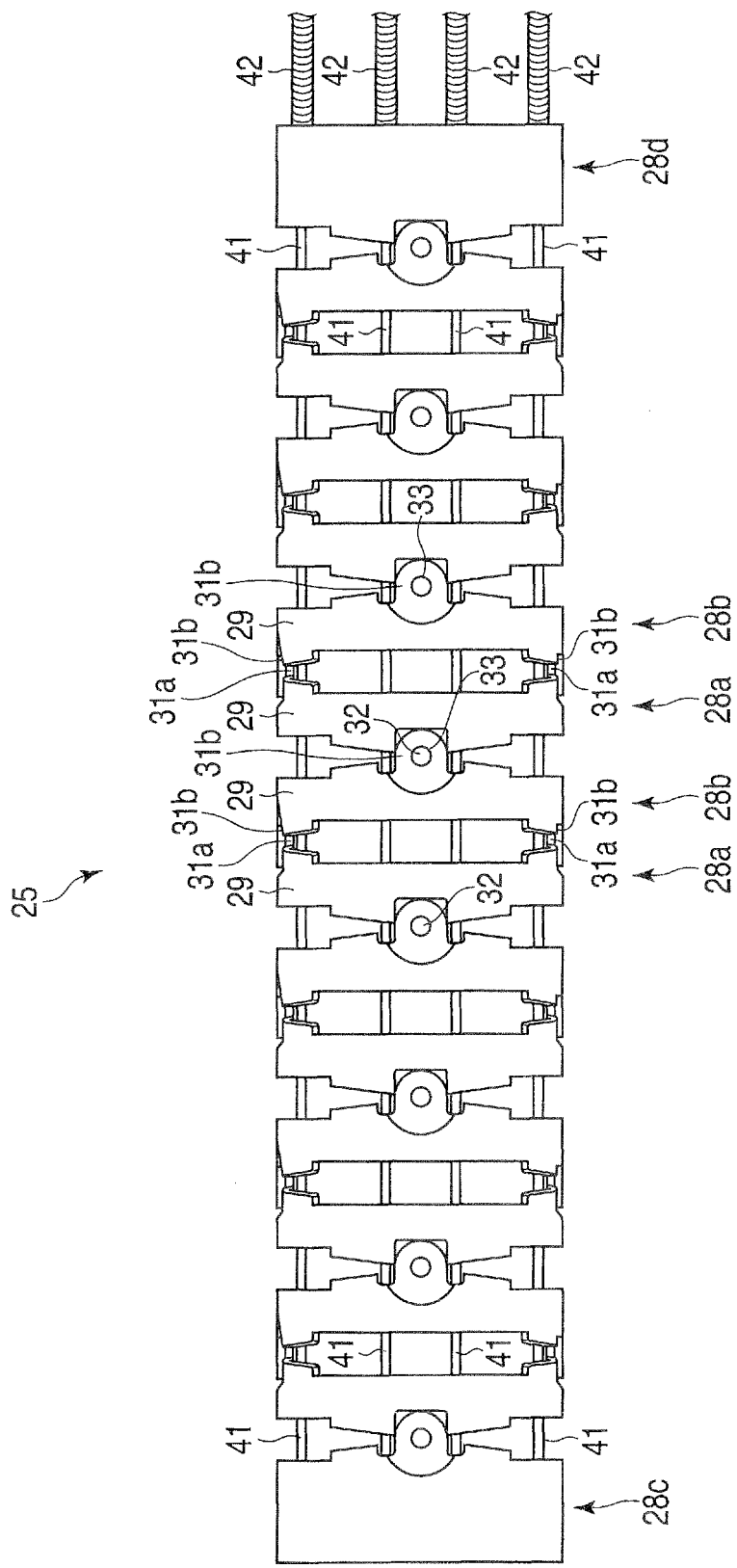
FIG. 2 is a side view showing a flexible tube unit according to the first embodiment of the invention.
Figure 3:
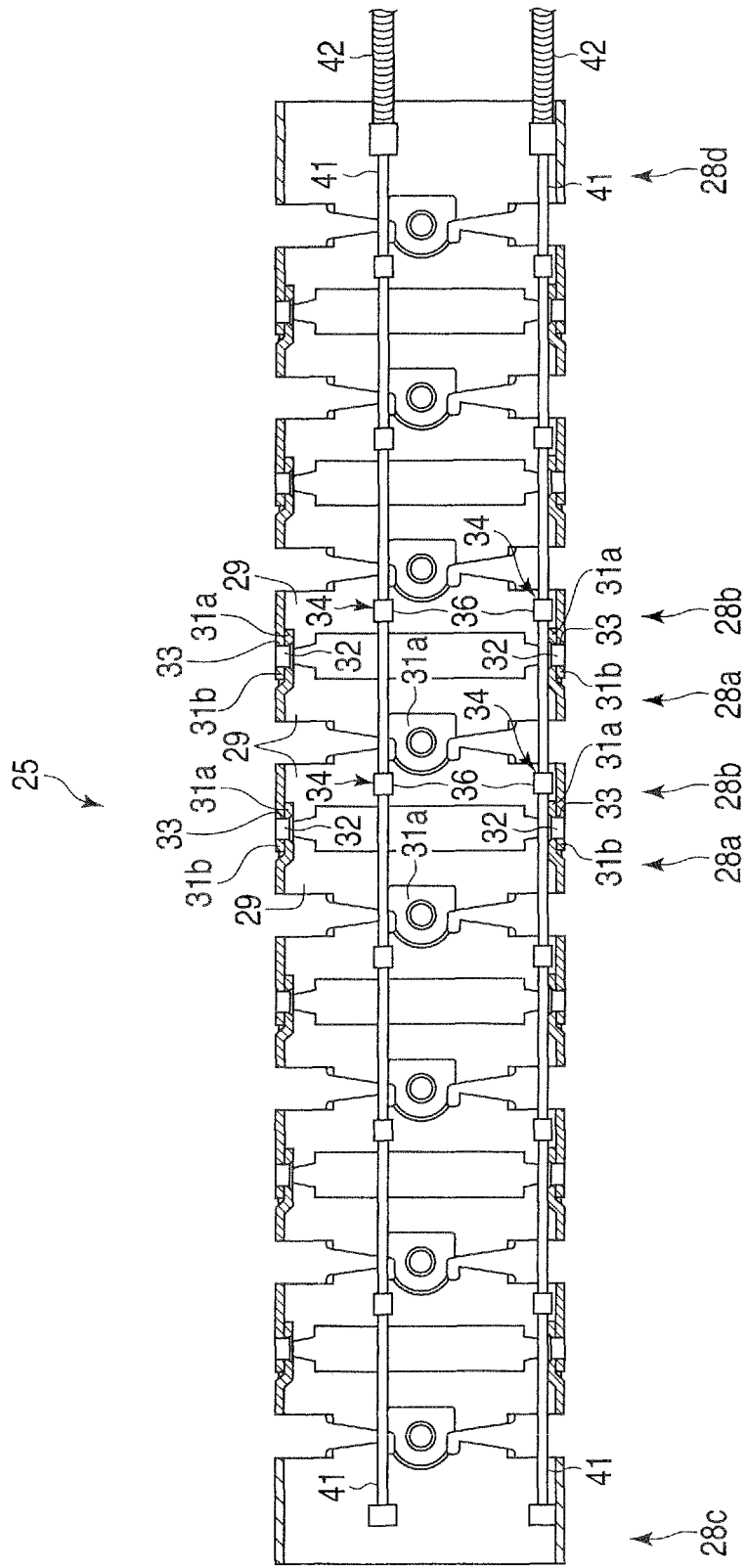
FIG. 3 is a longitudinal sectional view showing the flexible tube unit according to the first embodiment.

With reference to FIGS. 2 to 4, a great number of joint rings 28a and 28b are substantially coaxially connected to be pivotable in relation to one another, in the flexible tube of the flexible tube unit 25. That is, joint rings 28a and 28b of two types, which are a protrusion type and a hole type, are used as the joint rings 28a and 28b. In the flexible tube, the protrusion-type joint rings 28a and the hole-type joint rings 28b are provided alternately in an axial direction.

In each of the protrusion-type joint rings 28a and the hole-type joint rings 28b, pairs of tongue parts 31a and 31b are respectively protruded from two end surface parts of each cylindrical part 29. A pair of tongue parts 31a and 31b are symmetrical to each other about center axes of joint rings 28a and 28b.

A pair of tongue parts 31a and 31b on a top end side and a pair of tongue parts 31a and 31b on a base end side are positioned shifted by 90 degrees from each other along a circumferential direction of the joint rings 28a and 28b. For the protrusion-type joint rings 28a, the protrusion-type tongue parts 31a are of a plate type which is perpendicular to radial directions of the joint rings 28a, and are positioned inside of the cylindrical parts 29 in relation to the radial directions.

A protrusion part 32 is provided on an outer surface of each protrusion-type tongue part 31a along radial direction, so as to protrude outside in the radial direction. For the hole-type joint rings 28b each, the hole-type tongue parts 31b each form a flat plate shape perpendicular to the radial directions of the joint rings 28a, and are formed at the substantially same positions as the cylindrical parts 29 in relation to the radial directions.

A hole part 33 is formed to penetrate each of the hole-type tongue parts 31b in a radial direction thereof. For each adjacent ones of the protrusion-type joint ring 28a and hole-type joint ring 28b, the protrusion-type tongue part 31a and the hole-type tongue part 31b are layered on each other from inside to outside along radial directions.

The protrusion part 32 of the protrusion-type tongue part 31a is inserted in the hole part 33 of the hole-type tongue part 31b. The protrusion parts 32 each are respectively rotatable about center axes of the protrusion parts 32 at the hole parts 33.

Rotation of the protrusion parts 32 at such hole parts 33 causes the protrusion-type tongue parts 31a and hole-type tongue parts 31b to be pivoted in relation to each other, as well as the protrusion-type joint rings 28a and hole-type joint rings 28b to be pivoted in relation to each other.

Of the protrusion-type joint rings 28a, the pairs of protrusion-type joint rings 31a at the top end side and base end side are respectively arranged at left and right positions and at upper and lower positions. Of the hole-type tongue parts 31b, the pairs of the hole-type tongue parts 31b at the distal end side and at the base end side are respectively arranged at upper and lower positions and at left and right positions.

Therefore, in relation to predetermined one of the protrusion-type joint rings 28a, the hole-type joint rings 28b at the top end side and the base end side are respectively pivotable in the upward and downward directions and in the leftward and rightward directions. In relation to predetermined one of the hole-type joint rings 28b, the protrusion-type joint rings 28a at the top end side and at the base end side are pivotable in the leftward and rightward directions and in the upward and downward directions, respectively. The protrusion tube can be curved, as a whole, in the upward, downward, leftward, and rightward directions.

A top-end joint ring 28c provided at the most top end is of the hole type and is not provided with the pair of hole-type tongue parts 31b on the top end side. A base-end joint ring 28d provided at the most base end is of the protrusion type and is not provided with the pair of protrusion-type tongue part 31a on the base end side.

Figure 6:
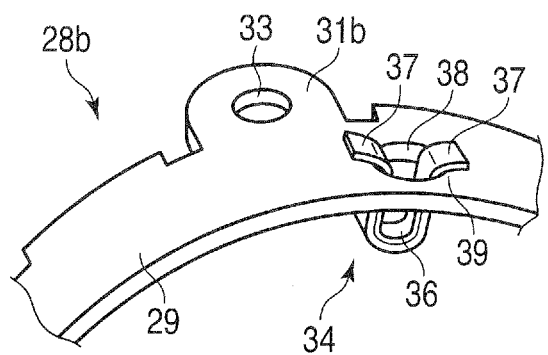
FIG. 6 is a perspective view showing a joint ring and the wire receiving member according to the first embodiment of the invention, viewed from outside in a radial direction.
Figure 7:
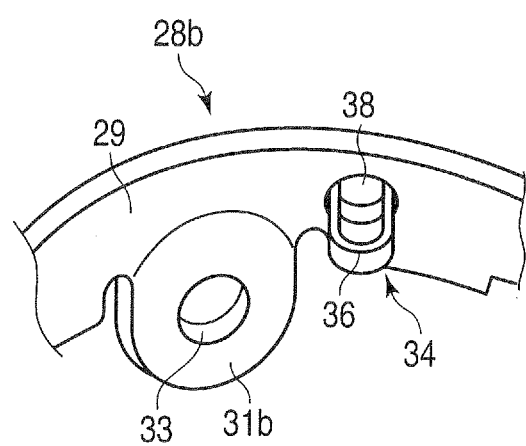
FIG. 7 is a perspective view showing the joint ring and the wire receiving member according to the first embodiment of the invention, viewed from inside in a radial direction.

With reference to FIGS. 5 to 7, a wire receiving member 34 as an operation-member receiving member is attached to each of the protrusion-type joint rings 28a. That is, a flat wire made of elastic stainless steel is used as a material of the wire receiving member 34.

In the flat wire, a cross section perpendicular to the longitudinal direction of the flat wire has a substantially rectangular shape whose edge parts at four corners each are smoothly r-shaped. The wire receiving member 34 is formed through a press bending process and a cutting process. The wire receiving member 34 has a substantial U-shape, and two upper ends of the U-shape are bent outwards in lateral directions.

In the wire receiving member 34, a wire insertion part 36 as an operation-member insertion part is formed by a U-shaped part in the middle of the flat wire. On the other side, an opening 38 having a substantially circular cross-section is formed to penetrate the cylindrical part 29 of each hole-type joint ring 28b. Further, the wire receiving member 34 is pressed into the opening 38 from outside to inside along the radial directions of the joint rings 28b.

The wire insertion part 36 of the wire receiving member 34 is protruded to inside along the radial directions of the joint rings 28b. An engagement part 37 of the wire receiving member 34 is engaged on an outer circumferential surface of the cylindrical part 29. Specifically, an engagement receiving surface 39 as an engagement receiving part is formed by a part surrounding the opening 38, on the outer circumferential surface of the cylindrical part 29.

The engagement part 37 is slidable on the outer circumferential surface of the cylindrical part 29, and the wire receiving member 34 is pivotable in relation to the cylindrical part 29 about a center axis of the opening 38, which extends in a radial direction of the joint ring 28b. In the cylindrical part 29, the opening 38 is formed at each of upper, lower, left, and right areas of the cylindrical part 29, which are slightly shifted from the upper, lower, left, and right positions in a circumferential direction. Therefore, the wire insertion parts 36 are provided at the upper, lower, right, and left areas.

Referring again to FIGS. 2 and 3, the angle wires 41 for curve operations in the upward, downward, leftward, and rightward directions are inserted through the upper, lower, left, and right wire insertion parts 36 of the hole-type joint rings 28b. Since the angle wires 41 are inserted into the wire insertion parts 36, the wire receiving members 34 are restricted from being pulled out of the opening parts 38.

The wire receiving members 34 are prevented from falling out of the joint rings 28b. Top ends of the angle wires 41 are fixed to inner circumference of the top-end joint ring 28c. On the base end side of the base-end joint ring 28d, the angle wires 41 are inserted into wire guides 42 made of coils. The top ends of the wire guides 42 are fixed to inner circumferential parts of the base-end joint ring 28d.

In the flexible part 23, a netty tube and an outer cover are covered one outer circumference of the flexible tube unit 25, and inner components such as a light guide, an imaging cable, a channel tube, and air and water feed tubes are inserted.

In the flexible part 23 in the present embodiment, as the upward and downward curve operation knobs 27u and 27l are rotated in a direction or another direction, the angle wires 41 for upward and downward curve operations are respectively pulled and relaxed or relaxed and pulled thereby to curve the flexible part 23 in an upward or downward direction.

The same as described also applies to the leftward and rightward directions. When an angle wire 41 is pulled/operated, the wire receiving members 34 are rotated in relation to the cylindrical parts 29 about center axes of the opening parts 38 extending in the radial directions of the joint rings 28b, as centers, depending on a positional relationship between the angle wire 41 and the wire insertion parts 36, and a state of load from the angle wire 41 to the wire insertion parts 36.

Simultaneously, the wire insertion parts 36 are elastically deformed. Therefore, resistance of the angle wire 41 against the pulling operation of the angle wire 41 is sufficiently reduced. With respect to the flat wire forming each wire insertion part 36, a cross-section perpendicular to the lengthwise direction of the flat wire is formed to have smoothly rounded edge parts respectively at four corners. Therefore, resistance of the angle wire 41 against pulling operations is sufficiently reduced. Therefore, the flexible part 23 can be operated to be smoothly curve.

In addition, a flat wire with excellent mass-productiveness is used as a material which forms the wire receiving members 34. As a processing method for forming the wire receiving members 34, press bending process and cutting process with excellent mass-productiveness are employed. Therefore, the wire receiving members 34 can be manufactured at low costs.

The wire receiving members 34 can be attached to the joint rings 28b, merely by pressing the wire receiving members 34 into the opening parts 38 of the cylindrical parts 29 of the joint rings 28b, and by engaging the engagement parts 37 of the wire receiving members 34 on the outer circumferential surfaces of the cylindrical parts 29. Process of attaching the wire receiving members 34 is thus extremely simplified. Further, the wire receiving members 34 are pressed into the opening parts 38, and therefore, the wire receiving members 34 can be retained on the cylindrical parts 29 by elasticity of the wire receiving members 34.

Therefore, the wire receiving members 34 are prevented from falling out of the joint rings 28b, when the angle wires 41 are inserted sequentially into the wire insertion parts 36. Accordingly, process of inserting the angle wires 41 is avoided from being complicated. Accordingly, the flexible part 23 can be manufactured at low costs.

With reference to FIGS. 8 to 13, the second embodiment of the invention will be described.

Figure 8:
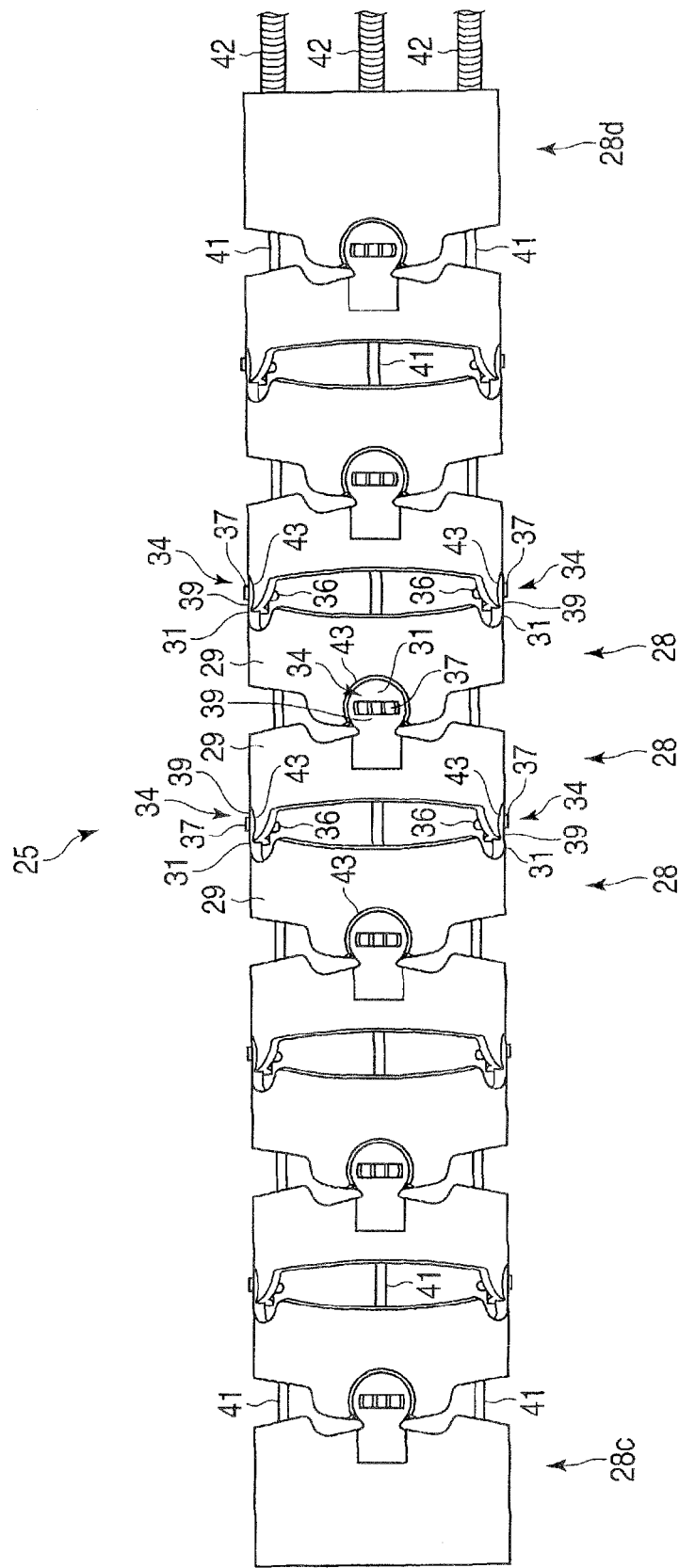
FIG. 8 is a side view showing a flexible tube unit according to the second embodiment of the invention.
Figure 9:
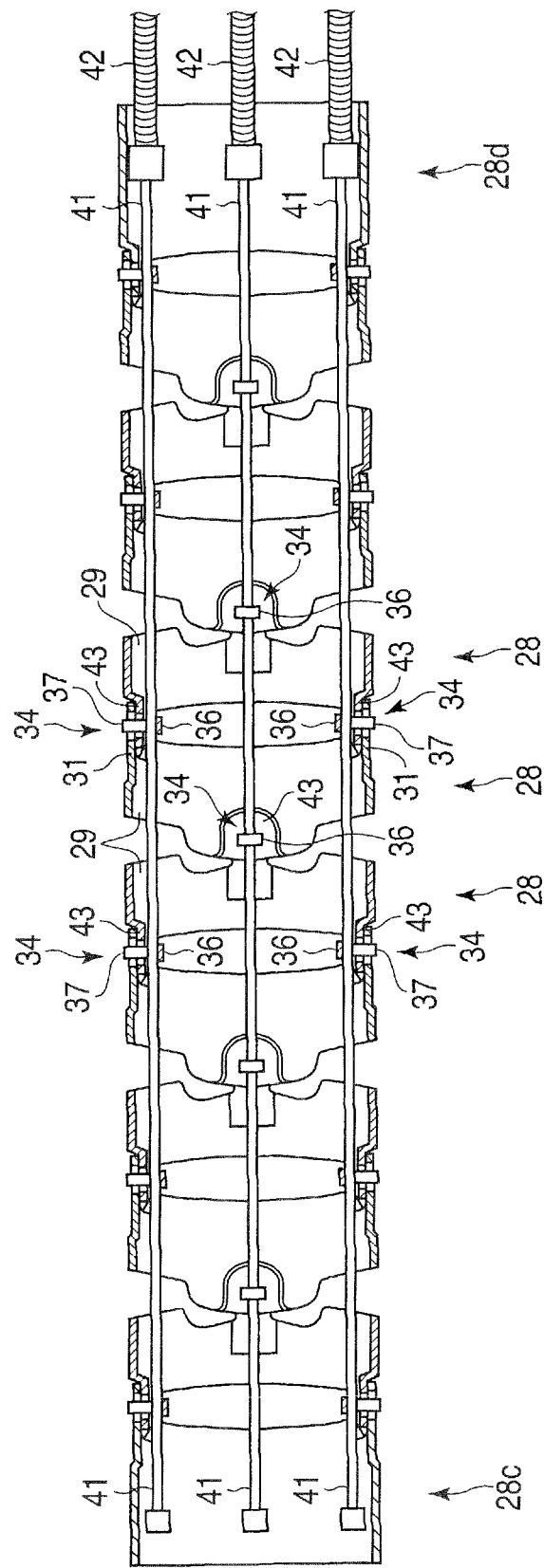
FIG. 9 is a longitudinal cross-sectional view showing a curved tube unit according to the second embodiment.

With reference to FIGS. 8 to 10, a flexible tube employs one kind of joint rings 28. The joint rings 28 each are provided with a pair of tongue receiving parts 43 as joint receiving parts which are formed at top-end-side parts of a cylindrical part 29. The pair of tongue receiving parts 43 are substantially symmetrical to each other about a center axis of the cylindrical part 29.

Each of the tongue receiving parts 43 forms a flat plate shape which is substantially perpendicular to radial directions, and is provided at the substantially same position as the cylindrical part 29 along the radial directions. The tongue receiving parts 43 each forms a concave shape which is concave from the top end side to the base end side. Here, the tongue receiving parts 43 are respectively formed of deformed parts which are obtained by inwardly deforming parts of the cylindrical part 29.

Support receiving walls 46 and slide receiving walls 44 as slide receiving surfaces are formed of the deformed parts. The support receiving walls 46 form inner side walls of the tongue receiving parts 43 along the radial directions, are substantially parallel to contact planes of the cylindrical part 29, and are positioned inside the cylindrical part 29 along the radial directions.

The slide receiving walls 44 of the tongue receiving parts 43 form outer circumferential walls of the tongue receiving parts 43, are substantially perpendicular to the tangent planes, and connect the support receiving walls 46 and the cylindrical parts 29 with each other. Here, the slide receiving walls 44 of the tongue receiving parts 43 form circular arcs where viewed in the radial directions.

The circular arcs are positioned to be symmetrical to each other about a symmetrical axis which extends through centers of the circular arcs in an axial direction of the cylindrical part 29. Central angles of the circular arcs are greater than 180 degrees, and two end parts of each of the circular arcs extend to the top end side over the centers of the circular arcs along the axial direction.

In the present embodiment, the central angles of the circular arcs are set to 270 degrees. In other words, the slide receiving walls 44 of the tongue receiving parts 43 form stopper parts having a parenthesis-like shape, which narrow the width of the tongue receiving parts 43 along a tangent direction perpendicular to the axial direction, at end parts of the tongue receiving parts 43.

A pair of tongue parts 31 as joint parts is formed at base-end parts of the cylindrical part 29. The pair of tongue parts 31 are symmetrical to each other about the center axis of the cylindrical part 29, and are positioned shifted by 90 degrees in a circumferential direction of the joint ring 28, in relation to the pair of tongue receiving parts 43. Each of the tongue parts 31 is provided to protrude from an annular surface at the base end of the cylindrical part 29, and forms a flat plate shape substantially perpendicular to a radial direction.

Each of the tongue parts 31 is provided at the same position as the cylindrical part 29 in relation to radial directions, and forms a convex shape which is convex from the top end side to the base end side. An inner wall of each of the tongue parts 31 in a radial direction forms a support wall 48, and an outer circumferential wall thereof forms a slide wall 49 as a slide surface. Here, the slide walls 49 of the tongue parts 31 each form a circular arc where viewed in a radial direction.

The circular arcs are positioned symmetrical to each other about a symmetrical axis which extends through centers of the circular arcs in an axial direction of the cylindrical part 29, where viewed in a radial direction.

The circular arcs have a radius substantially equal to that of the circular arcs of the slide receiving walls 44 of the tongue receiving parts 43. A central angle of each of the circular arcs each is slightly greater than an angle of a central angle of each of the tongue receiving parts 43 added with a double of a maximum pivotable angle between adjacent two joint rings 28.

For each adjacent two joint rings 28, two tongue parts 31 of the joint ring 28 in the top end side are engaged on two tongue receiving parts 43 of the joint ring 28 in the base end side. By the support walls 48 of the two tongue receiving parts 43, the support walls 48 of the two tongue parts 31 are supported in radial directions, and thereby restrict the two adjacent two joint rings 28 from shifting in diameter directions.

Further, the tongue parts 31 are prevented from falling toward the top ends in the axial direction from the tongue receiving parts 43 by the drop stopper parts having a parenthesis-like shape at the top ends of the tongue receiving parts 43. The adjacent two joint rings 28 are restricted from shifting in the axial direction from each other.

Further, by the slide receiving walls 44 of the tongue receiving parts 43, the slide walls 49 of the tongue parts 31 are supported to be slidable. Centers of the circular arcs of the tongue receiving parts 43 substantially correspond to centers of the circular arcs of the tongue parts 3. The tongue parts 31 can be pivoted about the centers of the circular arcs in relation to the tongue receiving parts 43.

The joint rings 28, in each of which the pair of tongue receiving parts 43 in the top end side and the pair of tongue parts 31 in the base one side are respectively provided at upper, lower, left, and right positions, and the joint rings 28, in each of which the pair of tongue receiving parts 43 in the top end side and the tongue parts 31 in the bottom end side are respectively provided at left, right, upper, and lower positions, are arranged alternately.

Therefore, in relation to predetermined one joint ring 28, other joint rings 28 in the top end side and in the base end side relative to a predetermined joint rings 28 can be pivoted respectively in leftward and rightward directions and in upward and downward directions or respectively in upward and downward directions and in leftward and rightward directions. The flexible tube as a whole can be curved in upward, downward, leftward, and rightward directions.

The pair of tongue parts 31 are not formed on the most-top-end joint ring 28c on the top end side thereof. The pair of tongue parts 31 are not formed on the most-base-end joint ring 28d on the base end side thereof.

Figure 12:
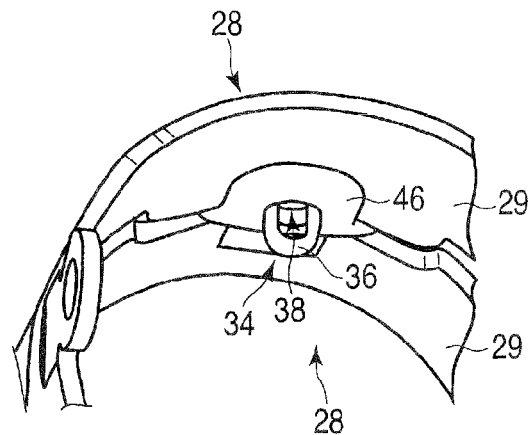
FIG. 12 is a perspective view showing the two adjacent joint rings and a wire receiving member according to the second embodiment of the invention, viewed from inside in a radial direction.
Figure 13:
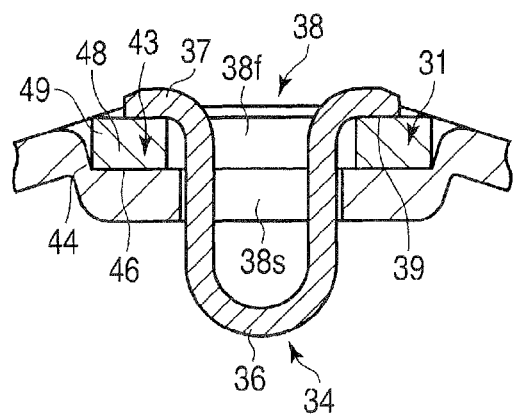
FIG. 13 is a cross-sectional view showing the two adjacent joint rings and the wire receiving member according to the second embodiment of the invention.

With reference to FIGS. 11 to 13, a wire receiving member 34 is attached to each of the joint rings 28. The present embodiment employs the same wire receiving members 34 as those in the first embodiment.

On the other side, a first opening part 38f having a circular cross-section is formed to penetrate the tongue part 31 of each joint ring 28 in a radial direction, coaxially with the circular arcs of the slide walls 49.

Further, a second opening part 38s having a circular cross-section is formed to penetrate the support receiving wall 46 of each tongue receiving part 43 in a radial direction, coaxially with the circular arcs of the slide receiving walls 44. The first opening part 38f and the second opening part 38s are positioned to be substantially coaxial with each other, and an inner diameter of the first opening part 38f and an inner diameter of the second opening part 38s are substantially equal to each other.

An opening part 38 is formed by the first and second opening parts 38f and 38s. The wire receiving member 34 is pressed into the opening 38 from outside to inside along a radial direction of the joint ring 28b. Wire insertion parts 36 are protruded to inside of the joint rings 28 in radial directions.

Further, engagement parts 37 of the wire receiving members 34 are engaged on outer surfaces of the tongue parts 31 in radial directions. Specifically, an engagement receiving surface 39 is formed by a part surrounding the opening 38, on the outer circumferential surface of each tongue part 31. The engagement part 37 is slidable on the outer circumferential surface of the tongue part 31 in a radial direction, and the wire receiving member 34 is pivotable in relation to the cylindrical part 29 about a center axis of the opening 38, which extends in the radial direction of the joint ring 28.

Specifically, the wire receiving members 34 each are pivotable in relation to the tongue parts 31, about a pivot axis for adjacent two joint rings 28 as a center. A set of a tongue receiving part 43 and a tongue part 31 contained in the tongue receiving part 43 is positioned at each of upper, lower, left, and right positions. The wire insertion part 36 is provided at each of upper, lower, left, and right positions.

Referring again to FIGS. 8 and 9, angle wires 41 for curve operations in upward, downward, leftward, and rightward directions are inserted through upper, lower, left, and right wire insertion parts 36 of the joint rings 28 each.

When a flexible part 23 in the present embodiment is operated to curve in upward, downward, leftward, and rightward directions, left, right, upper, and lower positions in the flexible part 23 are neutral positions which do not substantially change the total length in the axial direction. In the flexible part 23 in the present embodiment, the wire insertion parts 36 are provided at upper, lower, left, and right positions.

The angle wires 41 for upward, downward, leftward, and rightward curve operations are provided at upper, lower, left, and right positions. Therefore, when the flexible part 23 is operated to curve in the upward, downward, leftward, and rightward directions, the angle wires 41 for curve operations in the leftward, rightward, upward, and downward directions are positioned at neutral positions. Curve operations of the flexible part 23 are prevented from being hindered by any of the angle wires 41 which do not contribute to the curve operations.

The third embodiment of the invention will be described with reference to FIGS. 14 to 17.

Figure 14:
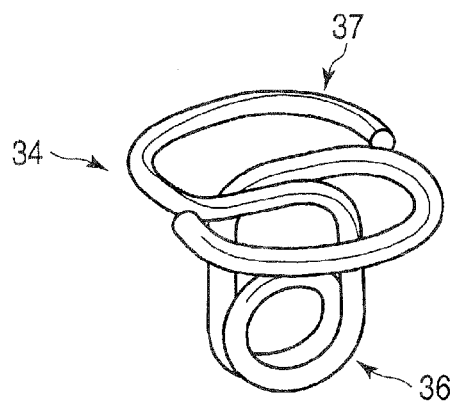
FIG. 14 is a perspective view showing a wire receiving member according to the third embodiment of the invention.

Referring to FIG. 14, the present embodiment employs a round wire as a material for wire receiving members 34. The wire receiving members 34 are formed of a round wire through bending process and cutting process by a spring processing apparatus for general purpose.

Thus, a round wire which has excellent mass-productiveness is used as a material for forming the wire receiving members 34. Bending process and cutting process are employed in a process method for forming the wire receiving members 34. Therefore, the wire receiving members 34 can be manufactured at low costs.

In the wire receiving members 34 each, an intermediate part of the round wire is wound round into a coiled shape, and a wire insertion part 36 is formed by the coiled part. By appropriately setting the number of turns of the coil part forming each wire insertion part 36, deformation properties such as rigidity against load can be optimally set with respect to the wire insertion parts 36.

Two ends of the round wire are extended in the same directions along tangent directions from two ends of the coil part in width directions, and are then bent to be perpendicular to the tangent directions. The two ends are further wound round in a plane perpendicular to the tangent directions, and an engagement part 37 is formed by the wound parts.

According to the present embodiment, one end of the round wire is extended linearly in a tangent direction from one end of the coil part in a width directions (the right end in the figure), and linearly extends from one side (the right side in the figure) to the other side (the left side in the figure) in the width direction.

The one end then extends from one side (the front side in the figure) to the other side (the deep side in the figure) in a length direction, and then extends from the other side (the left side in the figure) to the one side (the right side in the figure) in a width direction, so as to form a gently concave flexible shape to the other side (the deep side in the figure). The end then linearly extends from the other side (the deep side in the figure) to the one side (the front side in the figure).

The other end of the round wire is extended linearly in a tangent direction from the other end of the coil part in a width direction (the left end in the figure), and linearly extends from the other side (the left side in the figure) to the one side (the right side in the figure) in the width direction, in parallel with the other end side in a length direction, in relation to the one end of the round wire.

The other end then extends from the other side (the deep side in the figure) to the one side (the front side in the figure) in the length direction, and then extends from the one side (the right side in the figure) to the other side (the left side in the figure) in the width direction, so as to form a gently concave flexible shape to the one side (the front side in the figure). The end then linearly extends from the one side (the front side in the figure) to the other side (the deep side in the figure).

Figure 15:
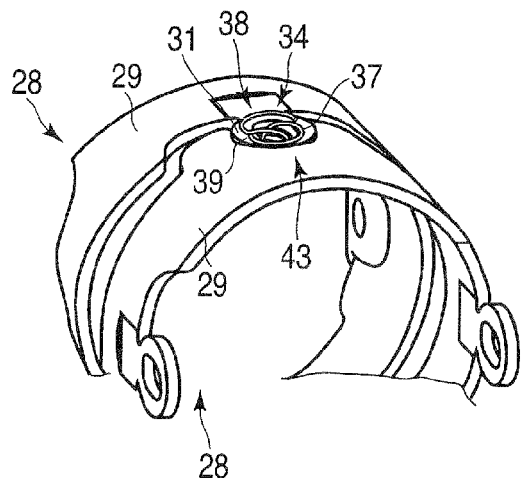
FIG. 15 is a perspective view showing two adjacent joint rings and the wire receiving member according to the third embodiment of the invention, viewed from outside in a radial direction.
Figure 16:
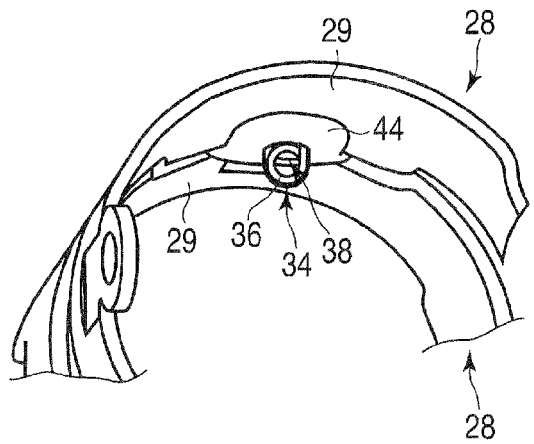
FIG. 16 is a perspective view showing the two adjacent joint rings and the wire receiving member according to the third embodiment of the invention, viewed from inside in a radial direction.
Figure 17:
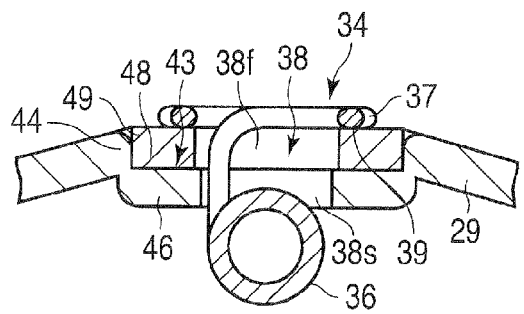
FIG. 17 is a cross-sectional view showing the two adjacent joint rings and the wire receiving member according to the third embodiment of the invention.

With reference to FIGS. 15 to 17, the flexible tube according to the present embodiment has the same configuration as the second embodiment, and the wire receiving members 34 are attached to the joint rings 28, as in the second embodiment. Here, when the wire receiving member 34 is pivoted in relation to the joint ring 28, the engagement part 37 formed of the wound part substantially parallel to the engagement receiving surface 39 is made slide on the engagement receiving surface 39 of the tongue part 31.

Therefore, in comparison with the first embodiment, friction resistance between the engagement receiving surfaces 39 and the engagement parts 37 is reduced, and the engagement parts 37 are made smoothly slide on the engagement receiving surfaces 39. Accordingly, the wire receiving members 34 are smoothly pivoted in relation to the joint rings 28.

With reference to FIG. 18, a modification to the third embodiment of the invention will be described.

Wire receiving members 34 according to the modification comprise engagement parts 37 each having a different shape from that of the wire receiving members 34 according to the third embodiment. Specifically, an end of a round wire is extended in a tangent direction from an end of a coil part in a width direction (the right end in the figure), and extends in a perpendicular plane from one side (the right side in the figure) to the other side (the left side in the figure), bent so as to form a convex half-circular arcuate shape to the other side in a length direction (the deep side in the figure).

The other end of the round wire is extended in a tangent direction from the other end (the left end in the figure) of the coil part in a width direction, and extends in the perpendicular plane from the other side (the left side in the figure) to the one side (the right side in the figure), bent so as to form a convex half-circular arcuate shape to the one side in a length direction (the front side in the figure).

The fourth embodiment of the invention will be described with reference to FIG. 19.

A flexible tube unit 25 according to the present embodiment is substantially the same as the flexible tube unit 25 according to the second embodiment. However, a first opening part 38*f* of each tongue part 31 has a greater inner diameter than that of a second opening part 38s of a support receiving wall 46 of each tongue receiving part 43.

An engagement part 37 of each wire receiving member 34 is contained in the first opening part 38f, and is engaged on an outer surface of the support receiving wall 46 of the tongue receiving part 43. Specifically, on an outer surface of each support receiving wall 46 in radial directions, an engagement surface 39 is formed as an engagement receiving part in the periphery of the second opening part 38s.

In the flexible part 23 in the present embodiment, the engagement parts 37 of the wire receiving members 34 are respectively contained in the first opening parts 38f of the tongue parts 31, and the wire receiving members 34 do not protrude outside in the radial directions.

Therefore, an outer diameter of the flexible part 23 can be reduced, and insertion ability of the insertion part 21 can be improved. Further, the wire receiving members 34 avoid hooking on a net-type tube nor an outer cover. When the net-type tube and outer cover are covered on the flexible tube unit 25, the net-type tube and outer cover are prevented from being damaged.

With reference to FIG. 20, a modification to the fourth embodiment of the invention will be described.

A flexible tube unit 25 according to the present modification is configured by employing the wire receiving members 34 according to the third embodiment in place of the wire receiving members 34 according to the second embodiment, in the flexible tube unit 25 according to the fourth embodiment.

The fifth embodiment of the invention will be described with reference to FIG. 21.

In the present embodiment, a soft resin layer 51 is formed by coating a film of soft resin, such as nylon, on a round wire 64 forming wire receiving members 34 by press molding or by coating and curing. Thereafter, the round wire 64 having the soft resin layer 51 is processed to form wire receiving members 34. Accordingly, the soft resin layer 51 is formed on wire insertion parts 36 of each wire insertion part 34.

Thus, the soft resin layer 51 is formed on the wire receiving members 34 by sequentially treating the round wire 64 before being processed, and the wire receiving members 34 with excellent mass-productiveness are achieved.

Also, the soft resin layer 51 functions as a modification layer. Specifically, when an angle wire 41 is pulled/operated, the soft resin layer 51 in addition to the wire insertion part 36 is elastically deformed, depending on a positional relationship between the angle wire 41 and a wire insertion part 36, and depending on a state of load from the angle wire 41 to the wire insertion parts 36.

Therefore, resistance of the angle wire 41 against the pulling operation is sufficiently reduced. Further, the soft resin layer 51 also functions as a protection layer, which prevents the wire insertion part 36 or inner components thereof from being damaged due to interference between the wire insertion part 36 and the inner component inside a curved tube.

Figure 22C:
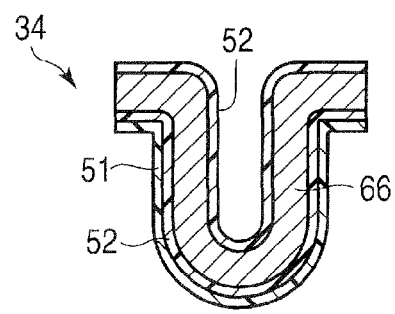
FIG. 22C is a cross-sectional view showing a wire receiving member according to the second modification to the sixth embodiment of the invention.

With reference to FIGS. 22A to 22C, the sixth embodiment according to the invention and a modification thereof will be described.

In the present embodiment, a soft resin layer 51 is formed on a surface of a flat wire 66 forming each wire receiving member 34, in the same manner as in the fifth embodiment, and a fixing lubricant, such as fluorocarbon resin, is coated on the other surface of the flat wire 66 by baking or coating, to form a solid lubricant layer 52.

Thereafter, the flat wire 66 having the soft resin layer 51 and solid lubricant layer 52 is processed, to form a wire receiving member 34 having the soft resin layer 51 outside and the solid lubricant layer 52 inside. At a wire insertion part 36 of each wire receiving member 34, the soft resin layer 51 is formed outside to face inner components, and the solid lubricant layer 52 is formed inside to face an angle wire 41.

With reference to FIG. 22B, the soft resin layer 51 may be formed on whole surfaces of the flat wire 66, and the solid lubricant layer 52 may be formed, layered on the soft resin layer 51 on the inside surface of the flat wire 66. In this case, soft resin is coated on the whole surfaces of the flat wire 66, and the solid lubricant may be thereafter coated only on an inside surface of the flat wire 66.

Alternatively, soft resin is coated on the whole surface of the flat wire 66, and the solid lubricant may then be coated on the whole surfaces of the flat wire 66. Thereafter, the solid lubricant layer on the outside surface of the flat wire 66 may be removed, with only the solid lubricant layer 52 remaining on the outside surface.

Otherwise, with reference to FIG. 22C, the solid lubricant layer 52 may be formed on the whole surfaces of the flat wire 66, and the soft resin layer 51 may be formed, layered on the solid lubricant layer 52 on the outside surface of the flat wire 66. In this case, the solid lubricant is coated on the whole surfaces of the flat wire 66, and the soft resin may be thereafter coated only on the outside surface of the flat wire 66.

Alternatively, the solid lubricant is coated on the whole surfaces of the flat wire 66, and the soft resin is coated on the whole surfaces of the flat wire 66. Thereafter, the soft resin layer on the inside surface of the flat wire 66 may be removed, with the soft resin layer 51 remaining on the outside surface.

Thus, the soft resin layer 51 and solid lubricant layer 52 can be formed on the wire insertion part 34 by sequentially treating the round wire 64 before being processed. Accordingly, the wire receiving members 34 with excellent mass-productiveness are achieved.

In addition, the solid lubricant layer 52 is formed on inside of the wire insertion part 36 which makes contact with an angle wire 41. Therefore, when an angle wire 41 is pulled/operated, resistance of the angle wire 41 against pulling operations is reduced.

Further, the soft resin layer 51 which functions as a protection layer is formed on outside of the wire insertion part 36 and prevents the wire insertion part 36 or inner components thereof from being damaged by interference between the wire Insertion part 36 and the inner components inside a curved tube.

Figure 23:
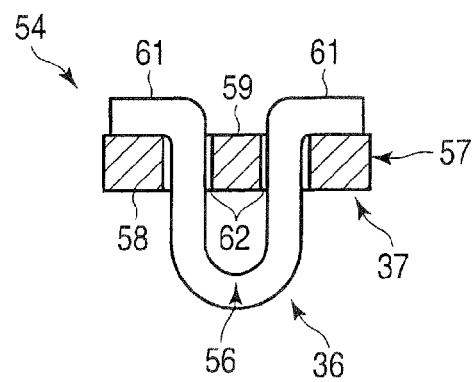
FIG. 23 is a cross-sectional view showing a wire receiving assembly according to the seventh embodiment of the invention.
Figure 24:
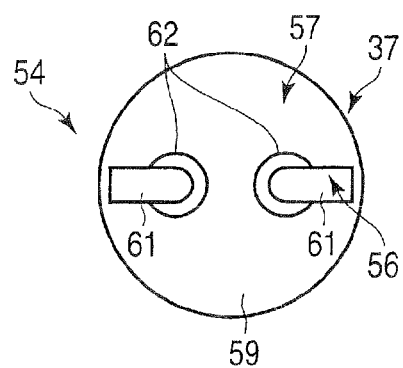
FIG. 24 is a top view showing the wire receiving assembly according to the seventh embodiment of the invention.

With reference to FIGS. 23 and 24, the seventh embodiment of the invention will be described.

In a wire receiving assembly 54 according to the present embodiment, each wire insertion part 36 is formed by a wire insertion member 56 made of a round wire, and each engagement part 37 is made of an engagement member 57 separate from the wire insertion member 56. Specifically, the wire insertion member 56 has a substantial U-shape. At two upper ends of the U-shape, lateral extending parts are extended outside in lateral directions from longitudinal extending parts.

Engagement parts 61 are respectively formed by the two ends. On the other side, the engagement members 57 each are of a disc type, and a pair of through holes 62 are formed in an axial direction in each engagement member 57. An engagement surface 58 to be engaged on a joint ring is formed of an end surface of the engagement member 57, and an engagement surface 59 is formed of the other end surface.

Further, two longitudinal extending parts of each wire insertion member 56 are respectively inserted into the two through holes 62 of the engagement member 57 from a side of the engagement surface 58 to a side of the engagement surface 59. The two lateral extending parts are arranged along the engagement surface of the engagement member 57. Thus, the wire insertion member 56 and the engagement member 57 are engaged on each other.

In the present embodiment, the engagement parts 37 are formed of the engagement members 57 which are separate from the wire insertion members 56 forming the wire insertion parts 36. Even a micro wire assembly 54 can be formed easily at low costs.

Figure 25:
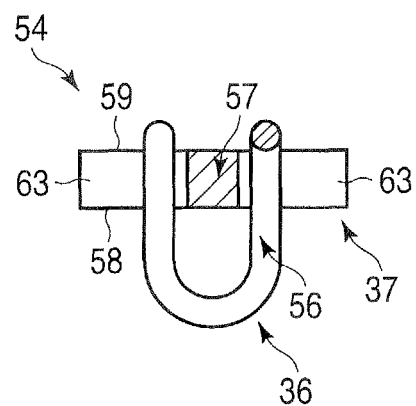
FIG. 25 is a cross-sectional view showing a wire receiving assembly according to a modification to the seventh embodiment of the invention.
Figure 26:
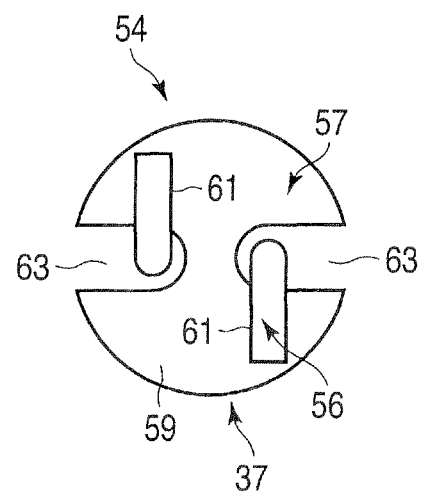
FIG. 26 is a top view showing the wire receiving assembly according to the modification to the seventh embodiment of the invention.

With reference to FIGS. 25 to 26, a modification to the seventh embodiment according to the invention will be described.

In the wire receiving assembly 54 according to the modification, the wire insertion members 56 each have a substantial U-shape. At two upper ends of the U-shape, a front extending part and a rear extending part are respectively extended from longitudinal extending parts.

Engagement parts 61 are respectively formed of the two ends. On the other side, a pair of notches 63 is formed in each of the engagement members 57. Each of the notches 63 forms a concave shape which is concave inside along a radial direction from an outer circumferential surface of the engagement member 57, and extends throughout a whole length of the engagement member 57 in an axial direction thereof. The pair of notches 63 is symmetrical to each other about a central axis of each engagement member 57.

Further, the two longitudinal extending parts of each wire insertion member 56 are engaged respectively in the two notches 63 of the engagement member 57. The front extending part and the rear extending part extend along the engagement surface 59 of the engagement member 57, in opposite directions to each other, perpendicularly to a depth direction of the notches 63. Thus, the wire insertion member 56 and the engagement member 57 are engaged on each other.

In the present modification, the notches 63 in place of the through holes 62 are formed in the engagement members 57. Therefore, difficult micro piercing process need not be performed, and even an extremely micro wire assembly 54 can be formed easily at low costs.

According to a preferred embodiment of the invention, a flexible endoscope part, comprising: an operation member pulled or operated to curve a flexible part; a plurality of joint rings connected substantially coaxially to be pivotable in relation to each other, the joint rings comprising at least one joint ring comprising an opening part which penetrates the joint ring in a radial direction thereof, and an engagement part formed around the opening part outside of the joint ring in the radial direction thereof; and an operation-member receiving unit which is inserted into the opening part from outside to inside in the radial direction of the joint ring, is formed by performing bending process on an elastic wire material, is protruded into inside of the joint ring, and comprises an operation-member insertion part where the operation member is inserted in, and an engagement part engaged on an engagement receiving part in a manner that the operation-member receiving unit is pivotable in relation to the joint ring about a rotation axis as a center extending in a substantially radial direction of the at least one joint ring.

In the flexible endoscope part according to the present embodiment, when an operation member is pulled/operated to curve the flexible part, the operation-member receiving unit is pivoted in relation to the joint rings and the operation-member insertion part is elastically deformed, depending on a positional relationship between the operation member and the operation-member insertion part and depending on a state of load to the operation-member insertion part from the operation member. Therefore, resistance of the operation member against pulling operations of the operation member decreases so that the flexible part can be easily and smoothly curved. In addition, the operation-member insertion part is formed by bending a wire material, a material with excellent mass-productiveness and a process method with excellent mass-productiveness are applied to the operation-member insertion part. The operation-member receiving unit can be attached to the joint ring merely by inserting the operation-member receiving unit into an opening part in the joint ring and by engaging an engagement part on an engagement receiving part. Thus, an attachment method with excellent mass-productiveness is adopted. Accordingly, the flexible endoscope part can be manufactured at low costs.

According to a preferred embodiment of the invention, the joint ring comprises a cylindrical part, the opening part is formed in the cylindrical part, and the engagement part is formed at an outside part of the cylindrical part in a radial direction thereof.

According to a preferred embodiment of the invention, the plurality of joint rings comprise first and second joint rings, the first joint ring comprises a first cylindrical part, and a joint part which is formed on the first cylindrical part in a side of the second joint ring and forms a convex shape convex from a side of the first joint ring to the side of the second joint ring, the second joint ring comprises a second cylindrical part, a joint receiving part, and a support receiving part, the support receiving part being formed on the second cylindrical part in the side of the first joint ring, forming a concave shape concave from the side of the first joint ring to the side of the second joint ring, and containing the joint part, and the support receiving part being provided in parallel with radial directions of the first and second joint rings; the joint part comprises a slide surface and a support surface, the slide surface being formed by an outer circumferential surface of the joint part, provided at least in two side parts of the joint part, with respect to circumferential directions of the first and second joint rings, and forming a circular arc viewed in the radial direction, and the support surface being formed by a side surface of the joint part in the radial direction, the joint receiving part comprises a side receiving surface, which forms an outer circumferential surface of the joint receiving part, is provided on each of at least two side parts of the joint receiving part with respect to the circumferential directions, forms a circular arc, and slidably supports the slide surface, the circular arc having a radius substantially equal to a radius of the slide surface, where viewed in the radial directions, extending more to the side of the first joint ring than a center of the circular arc with respect to axial directions of the first and second joint rings, in the two side parts, the support receiving part comprises a support receiving surface which supports the support surface in the radial directions, the first joint ring comprises a first opening part which penetrates the joint part in the radial directions and is substantially coaxial to the circular arc of the slide surface, the second joint ring comprises a second opening part which penetrates the support receiving part in the radial directions and is substantially coaxial to the circular arc of the slide receiving surface, the opening part is formed by the first and second opening parts, and the engagement part is formed around the first or second opening part in an outside part of the joint part or the support receiving part in the radial directions.

According to a preferred embodiment of the invention, the joint part is positioned outside the support receiving part in the radial directions, and the engagement part is formed on the joint part.

According to a preferred embodiment of the invention, the joint part is positioned outside the support receiving part in the radial directions, and the engagement part is contained in the first opening part, and the engagement part is formed on the support receiving part.

In the flexible endoscope part of the present embodiment, the engagement part is contained in the first opening part, and the operation-member receiving unit does not protrude outside from the joint ring in radial directions. An outer diameter of the flexible part can be reduced, and insertion ability of the endoscope can be improved. In addition, the operation-member receiving unit avoids hooking on a member covered on an outer circumferential part of the joint ring, and the covering member is prevented from being damaged.

According to a preferred embodiment of the invention, the wire material has a smooth outer circumferential shape on a cross-section perpendicular to a lengthwise direction of the wire material.

In the flexible endoscope part according to the present embodiment, the wire material has a smooth outer circumferential shape on a cross-section perpendicular to a lengthwise direction of the wire material, for this reason, the resistance to traction operation of final the operation-member decreases.

According to a preferred embodiment of the invention, the operation-member receiving unit is pressed into the opening part.

In the flexible endoscope part of according to the present embodiment, the operation-member receiving unit is pressed into the opening part, and the operation-member receiving unit is stably held on the joint ring. Therefore, when the operation member is inserted in the operation-member insertion part after attaching the operation-member receiving unit to the joint ring, the operation-member receiving unit is prevented from falling. Accordingly, complication of insertion process for the operation member is avoided.

According to a preferred embodiment of the invention, the operation-member insertion part has a U-shape where viewed in an insertion direction of the operation member.

The flexible endoscope part according to the present embodiment, the operation-member insertion part is U-shaped, and has a simple configuration. Therefore, the operation-member receiving unit can be easily formed at low costs.

According to a preferred embodiment of the invention, the operation-member insertion part forms a coil shape which extends in an insertion direction of the operation member.

In the flexible endoscope part according to the present embodiment, the operation-member insertion part is coiled, and deformation property of the operation-member insertion part can be optimally set by appropriately setting the number of turns of the coiled part.

According to a preferred embodiment of the invention, the wire material is a round wire or a deformed wire or, preferably, a flat wire.

In the flexible endoscope part according to the present embodiment, a round wire or a deformed wire or, preferably, a flat wire, which is excellent in mass-productiveness and processability is used as the wire material. The wire receiving unit can be manufactured at satisfactorily low costs.

According to a preferred embodiment of the invention, the wire material includes a deformed layer or, preferably, an elasticity resin layer which is covered on a surface of the wire material.

In the flexible endoscope part according to the present embodiment, a deformed layer is coated on a surface of the wire material, and the deformed layer is formed on the wire insertion part. Therefore, resistance of the operation-member against pulling operations is reduced owing to deformation effect of the deformed layer. Further, by continuously coating the deformed layer on the wire material as a material forming the wire insertion part, the deformed layer is formed on the wire insertion part, and the wire insertion part with excellent mass-productiveness is achieved.

According to a preferred embodiment of the invention, the wire material includes a protection layer or, preferably, a soft resin layer which is covered on a surface of the wire material.

In the flexible endoscope part according to the present embodiment, a protection layer is coated on a surface of the wire material. Since the protection layer is formed on the wire insertion part, an inner component of the flexible endoscope part is prevented from being damaged, owing to protection effect of the deformed layer. Further, by continuously coating the protection layer on the wire material as a material forming the wire insertion part, the protection layer is formed on the wire insertion part, and the wire insertion part with excellent mass-productiveness is achieved.

According to a preferred embodiment of the invention, the wire material includes a solid lubricant layer or, preferably, a fluorocarbon resin layer which is covered on a surface of the wire material.

In the flexible endoscope part according to the present embodiment, the solid lubricant layer is coated on a surface of the wire material, and the solid lubricant layer is formed on the wire insertion part. Therefore, resistance of the operation member against pulling operations is reduced owing to lubrication effect of the solid lubricant layer. Further, by continuously coating the solid lubricant layer on the wire material as a material forming the wire insertion part, the solid lubricant layer is formed or the wire insertion part, and the wire insertion part with excellent mass-productiveness is achieved.

According to a preferred embodiment of the invention, the engagement part is formed by performing bending process on a wire material common to the wire material forming the operation-member insertion part, and the operation-member receiving unit is an operation-member receiving member which is formed by an integral wire material.

In the flexible endoscope part according to the present embodiment, the operation-member receiving unit is formed of an integral wire material, and therefore, the operation-member receiving unit can be formed easily at low costs.

According to a preferred embodiment of the invention, the engagement part is formed by an engagement member different from the wire material forming the operation-member insertion part, and the operation-member receiving unit is an operation-member receiving assembly which is formed by the wire material and the engagement member.

According to a preferred embodiment of the invention, the engagement member comprises a pair of through holes, and the operation-member insertion part comprises a pair of engagement parts which are respectively formed of two ends of the wire material forming the operation-member insertion part, are respectively inserted into the pair of through holes, and are engaged on the engagement member, also, the engagement member comprises a pair of notches, and the operation-member insertion part comprises a pair of engagement parts which are respectively formed of two ends of the wire material forming the operation-member insertion part, are respectively inserted into the pair of notches, and are engaged on the engagement member.

In the flexible endoscope part according to the present embodiment, the operation-member insertion part and the engagement part are formed of separate members in the operation-member receiving unit. Therefore, even a micro operation-member receiving unit can be formed easily at low costs.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible endoscope part, comprising:
a longitudinally extending operation member which is operable to curve the flexible endoscope part;
a plurality of joint rings connected substantially coaxially to be pivotable in relation to each other; and
a plurality of operation-member receiving units, each of which comprises an elastic wire material and is formed by a bending process;
wherein each of the plurality of joint rings comprises a tongue part and a tongue receiving part;
wherein the tongue part and the tongue receiving part of respective adjacent ones of the joint rings are arranged to overlap;
wherein each of the joint rings comprises a plurality of openings which penetrate the joint ring in a radial direction thereof, wherein the plurality of openings are respectively provided in the tongue part and the tongue receiving part of the joint rings, such that each opening is provided in an overlapping portion of the tongue part and the tongue receiving part of adjacent joint rings, and an engagement receiving part formed around the opening in the tongue part on an outer surface of the joint ring with respect to the radial direction thereof;
wherein each of the plurality of operation-member receiving units is inserted into a respective pair of overlapping openings of the tongue part and tongue receiving part of adjacent joint rings, from outside to inside in the radial direction of the adjacent joint rings, wherein the operation-member receiving unit is inserted through the pair of overlapping openings to penetrate the overlapping portion of the tongue part and the tongue receiving part, so as to connect the adjacent joint rings together, such that the operation-member receiving unit acts as a connecting tool for connecting the adjacent joint rings;
wherein each operation-member receiving unit comprises a bent operation-member insertion part having two ends and through which the operation member is inserted and longitudinally extends within the joint rings, and an engagement part which is formed so as to bend and extend out in a circumferential direction of the adjacent joint rings from both ends of the operation-member insertion part, and which is engaged with a respective engagement receiving part of the joint rings such that the operation-member receiving unit is pivotable in relation to the joint rings about a rotation axis extending substantially in the radial direction of the joint rings; and
wherein the operation-member receiving unit is retained in the opening by its elasticity.

2. An endoscope comprising the flexible endoscope part of claim 1.

* * * * *